United States Patent
Van Asbrouck

(10) Patent No.: US 8,866,106 B2
(45) Date of Patent: Oct. 21, 2014

(54) PRODUCT MARKING

(75) Inventor: Johan Gaston Marie Van Asbrouck, Phichit (TH)

(73) Assignee: Rhino Research Europe B.V., Aalten (NL)

( * ) Notice: Subject to any disclaimer, the term of this patent is extended or adjusted under 35 U.S.C. 154(b) by 527 days.

(21) Appl. No.: 13/320,534

(22) PCT Filed: May 12, 2010

(86) PCT No.: PCT/NL2010/050274
§ 371 (c)(1),
(2), (4) Date: Apr. 2, 2012

(87) PCT Pub. No.: WO2010/131959
PCT Pub. Date: Nov. 18, 2010

(65) Prior Publication Data
US 2012/0181448 A1 Jul. 19, 2012

(30) Foreign Application Priority Data

May 14, 2009 (EP) .................................... 09160309

(51) Int. Cl.
*G01J 1/58* (2006.01)
*A01N 25/26* (2006.01)
*C09K 11/74* (2006.01)
*C09K 11/58* (2006.01)
*C09K 11/77* (2006.01)
*G01N 21/91* (2006.01)
*G01N 21/85* (2006.01)
*G01N 21/84* (2006.01)
*G01N 21/64* (2006.01)

(52) U.S. Cl.
CPC .... *C09K 11/7792* (2013.01); *G01N 2021/8592* (2013.01); *C09K 11/7421* (2013.01); *C09K 11/584* (2013.01); *C09K 11/7795* (2013.01); *G01N 2021/8427* (2013.01); *G01N 21/91* (2013.01); *G01N 2021/646* (2013.01)

USPC .................. 250/458.1; 250/361 R; 504/100; 47/57.6

(58) Field of Classification Search
CPC ................ G01N 2021/646; G01N 2021/8592; G01N 2021/8422; G01N 2021/8427; G01N 21/91; C09K 11/7792; C09K 11/7795; C09K 11/7421; C09K 11/584
USPC ............ 250/302, 458.1; 428/690; 106/18.31; 504/100; 424/410; 47/57.6; 427/4
See application file for complete search history.

(56) References Cited

U.S. PATENT DOCUMENTS

| | | | | |
|---|---|---|---|---|
| 5,750,996 | A | * | 5/1998 | Drennen et al. ............ 250/341.2 |
| 5,900,944 | A | * | 5/1999 | Mawby ......................... 356/425 |
| 2006/0163491 | A1 | * | 7/2006 | Angal et al. ................. 250/458.1 |
| 2006/0236604 | A1 | * | 10/2006 | Hesse et al. ..................... 47/57.6 |
| 2010/0154299 | A1 | * | 6/2010 | Kobayashi et al. ............. 47/57.6 |
| 2011/0258924 | A1 | * | 10/2011 | Van Asbrouck et al. ........ 47/57.6 |

FOREIGN PATENT DOCUMENTS

| | | |
|---|---|---|
| EP | 0 619 062 | 10/1994 |
| EP | 1 262 778 | 12/2002 |
| EP | 2 120 187 | 11/2009 |
| WO | WO-2009/053391 | 4/2009 |

OTHER PUBLICATIONS

International Search Report for PCT/NL2010/050274, mailed Aug. 19, 2010, 2 pages.

* cited by examiner

*Primary Examiner* — David Porta
*Assistant Examiner* — Yara B Green
(74) *Attorney, Agent, or Firm* — Morrison & Foerster LLP

(57) ABSTRACT

The present invention relates to a method for the authentication of a product, comprising providing said product with at least one marker, wherein said marker is a phosphorescent marker selected from a set of m phosphorescent markers each having a different emission spectrum, wherein m is an integer equal or greater than 3, and wherein said marker is provided at an amount that results in a phosphor-specific emission below background radiation emitted from said product.

15 Claims, No Drawings

PRODUCT MARKING

CROSS-REFERENCE TO RELATED APPLICATIONS

This application is the national phase of PCT application PCT/NL2010/050274 having an international filing date of 12 May 2010, which claims benefit of European patent application No. 09160309.2 filed 14 May 2009. The contents of the above patent applications are incorporated by reference herein in their entirety.

FIELD OF THE INVENTION

The present invention is in the field of product coating, more in particular to methods for the analysis the quality of the coating or coating process of a product, in particular a seed. The present invention further relates to seed coating compositions, to coated seeds obtained by use of the coating composition, and to a kit of parts for applying a seed coating composition to a seed product.

BACKGROUND OF THE INVENTION

In order to optimize germination percentage and seedling establishment, seed disease and lack of nutrients and water should be minimized during the early establishment of a plant. It is possible to control diseases in germinating seeds by coating the seed before planting with, for instance, pesticides. Seed coating is a technique in which several materials such as fertilizers, nutrients, moisture attractive or repulsive agents, plant growth regulators, rhizobium inoculum, and pestcides are combined with a binder and applied to the surface of the seed. Seed coating leads to increase benefits in seed industry.

A number of patents describe processes for the marking and coating of seeds by active ingredients and film forming compositions. U.S. Pat. No. 5,087,475 discloses a process for the film-coating of materials using a water- and gas-permeable, adhesive film-forming substance, which consists of spraying the film-forming substance on seed materials and drying the seed materials. U.S. Pat. No. 5,470,581 discloses a process for providing an aqueous film-coating from a combination of maltodextrin and cellulosic polymers for and agricultural seeds. The aqueous suspension can be applied by spraying. U.S. Pat. No. 5,849,320 discloses a process for coating a seed with an insecticide. U.S. Pat. Nos. 4,853,429 and 4,881,343 describe an aqueous medium containing a dye or pigment and a binder resin composed of the salt of chitosan and an organic acid for seed colouring. U.S. Pat. No. 5,746,022 discloses a seed colour coating composition containing a solvent, a binder, a colourant and other optional additives. U.S. Pat. No. 4,272,417 discloses a liquid seed coating composition containing a binding agent, an active ingredient and a colouring agent in a liquid medium including water and a polyol. U.S. Pat. No. 4,368,591 discloses seeds that are coated with an active ingredient and between 0.035 and 1.8 grams of titanium dioxide per kilogram of seed. WO 99/66784 discloses a process for coating seeds with a thin coating of a pigment that selectively allows light rays having wavelengths of about 570 to 700 nm to pass there through.

It is important that all components are present on the seed in correct amounts, however, once the seed is coated it is difficult to establish if all components are in fact present in the coating. However, none of the above disclosure teaches how the efficiency of the coating process can be evaluated.

There is however a need to check the quality of the final coating, for instance by confirming the presence of any one individual component of multi-component coating composition, and the relative amount of one of more components.

There is also a need to check the quality of the coating process, i.e. to monitor the efficacy and accuracy of the seed treatment process.

In particular there is a need to monitor the amount of treatment substance successfully loaded on an individual seed as a result of a coating process, which amount is referred to as the distribution, or on a set amount (e.g. per kilogram) of seed as a result of a coating process, which amount is referred to as the recovery.

It is an aim of the present invention to provide means and methods for assessing the quality of a seed coat and the quality and performance of a seed coating process. In alternative embodiments, it is an aim of the present invention to provide proof of origin of seeds or preservation of the identity of the seed.

SUMMARY OF THE INVENTION

The present inventors have now found that the use of phosphorescent markers can overcome the problems of the prior art systems and provide a possibility to assess the quality of a seed coat and the quality and performance of a seed coating process In a first aspect, the present invention now provides a method for analysis of a surface coating process of a product surface or for the analysis of the surface coating resulting therefrom on a product, said surface coating process comprising the application of a coating substance to the outer surface of said product, wherein said analysis comprising the steps of:

producing a surface coating by applying to the surface of said product a coating composition comprising an aqueous suspension comprising a coating substance and further comprising a marker system comprising at least one phosphorescent marker, wherein the coating substance and the phosphorescent marker are present at a fixed ratio, and wherein the marker system serves as an internal standard to the coating substance, optionally drying said coating composition;

quantitatively or qualitatively measuring the intensity of said at least one phosphorescent marker in said surface coating on the surface of said product; and determining from the measured intensity of the phosphorescent marker the amount of coating substance on said product surface in order to assess the quality of said surface coating or of said surface coating process.

In a preferred embodiment of said method, said product is a seed and wherein said surface coating process comprises the application of a desired amount or concentration of a seed coat to said seed.

In another preferred embodiment of said method, said fixed ratio of the phosphorescent marker to the coating substance is in the range of $1:1\times10^1$ to $1:1\times10^9$, preferably in the range of $1:1\times10^4$ to $1:1\times10^7$, still more preferably in the range of $1:1\times10^5$ to $1:1\times10^6$.

In another preferred embodiment of said method, said marker system, is provided at an amount that results in a phosphor-specific emission below background radiation or autofluorescence emitted from said product.

In another preferred embodiment of said method, said background radiation comprises light having a wavelength equal to the excitation wavelength and/or emission wavelength of said phosphor.

In another preferred embodiment of said method, said light having a wavelength equal to the emission wavelength of said phosphor is autofluorescence under daylight conditions (400-20000 lux).

In another preferred embodiment of said method, said marker is applied to said surface at an amount of between 0.001 and 999 ppm, preferably at an amount of between 0.01 and 99 ppm, more preferably at an amount of between 0.1 and 10 ppm.

In another preferred embodiment of said method, the intensity of said marker is used to monitor the surface coating process during the application of the coating substance.

In another preferred embodiment of said method, the quality of said surface coating process is the recovery and/or distribution of coating substance on the surface of said product.

In another preferred embodiment of said method, said phosphorescent marker (also commonly referred to as "glow-in-the dark" marker) is selected from the group consisting of europium-, dysprosium-, and/or terbium-doped lutetium orthophosphate ($LuPO_4$:Eu/Dy/Tb); europium-, dysprosium-, and/or terbium-doped strontium aluminate ($SrAl_2O_4$:Eu/Dy/Tb); europium-, dysprosium-, and/or terbium-doped strontium magnesium silicate ($Sr_2MgSi_2O_7$:Eu/Dy/Tb), copper-activated zinc sulphide (ZnS:Cu); silver-activated zinc sulphide (ZnS:Ag); copper-activated zinc-cadmium sulphide ((Zn,Cd)S:Cu) and bismuth-activated calcium-strontium sulphide ((Ca,Sr)S:Bi).

In another preferred embodiment of said method, said coating substance is selected from the group consisting of anti-microbial agent, pesticide, fungicide, herbicide, rodenticides, nematocides, miticides, bird, repellent, insect repellent, nutrient (including N, P or S), organic fertilizer, lime, trace element, hormone, vitamin, fertilizer, pigment, dye, and urea.

In another aspect, the present invention provides a seed coating composition comprising an aqueous suspension of a seed coating substance and further comprising a marker system comprising at least one phosphorescent marker, wherein the coating substance and the phosphorescent marker are present at a fixed ratio of $1:1\times10^1$ to $1:1\times10^8$, preferably in a ratio of $1:1\times10^4$ to $1:1\times10^6$, and wherein the marker system serves as an internal standard to the coating substance.

In a preferred embodiment of said seed coating composition, said phosphorescent marker is provided as phosphor particles having an average particle size of between 10 and 40 microns, preferably whose afterglow half-life is less than 5 minutes.

In another preferred embodiment of said seed coating composition, said phosphorescent marker is selected from the group consisting of europium-, dysprosium-, and/or terbium-doped lutetium orthophosphate ($LuPO_4$:Eu/Dy/Tb); europium-, dysprosium-, and/or terbium-doped strontium aluminate ($SrAl_2O_4$:Eu/Dy/Tb); europium-, dysprosium-, and/or terbium-doped strontium magnesium silicate ($Sr_2MgSi_2O_7$:Eu/Dy/Tb), copper-activated zinc sulphide (ZnS:Cu); silver-activated zinc sulphide (ZnS:Ag); copper-activated zinc-cadmium sulphide ((Zn,Cd)S:Cu) and bismuth-activated calcium-strontium sulphide ((Ca,Sr)S:Bi).

In another preferred embodiment of said seed coating composition, said coating substance is selected from the group consisting of antimicrobial agent, pesticide, fungicide, herbicide, rodenticides, nematocides, miticides, bird, repellent, insect repellent, nutrient (including N, P or S), organic fertilizer, lime, trace element, hormone, vitamin, fertilizer, pigment, dye, and urea.

In another aspect, the present invention provides a coated seed comprising a seed coat produced by applying a seed coating composition according to the invention and optional drying of said seed coating composition as defined above.

In another aspect, the present invention provides a kit of parts, comprising (a) a seed coating composition according to any one of claims 12-15, wherein said marker system is provided in a container optionally in combination with the coating substance, and (b) a detector system for detecting the presence of said phosphorescent marker on a seed surface, said detector comprising an excitation source and a detector for detecting phosphorescence emitted from said phosphorescent marker, and further comprising a control unit for switching said excitation source between an on position and an off position and for activating said detector when the excitation source is switched off after excitation of said seed thereby measuring phosphorescence emission, said kit further optionally comprising (c) a carrier or diluent for carrying the marker and or applying the marker to the product and/or (d) instructions for the application of said marker system to a product, for operating said detector and for the analysis of said marked product using the method of the present invention as described above.

DETAILED DESCRIPTION OF THE INVENTION

The term "product", as used herein, refers in principle to any type of product that can be marked with molecular markers. For instance, the product may be a fluid or solid product. Suitable solid product may be products of manufacture or natural products. Products of manufacture may for instance comprise clothings, shoes, "batch of product" or "type of product".

The term "seed", as used herein, refers to both horticultural and agricultural seed. Agricultural seeds include the seed of grass, legume, forage, cereal and fiber crops. Agricultural seeds include for instance seeds from grasses or cereal crops, including corn, wheat, barley, sorghum etc.; or seeds from vegetable crops such as carrot, onion, and tomato. Horticultural seeds include such seeds of crops, especially flowers, fruit, and vegetables generally grown in gardens or greenhouses. Such crops include pepper, melon, tomato, cucumber etc.

The term "luminescence", as used herein, refers to the process in which light is emitted from a material at a different wavelength than that which is absorbed. It is an umbrella term covering both fluorescence and phosphorescence.

The term "fluorescence", as used herein, refers to a luminescence phenomenon in which electron de-excitation occurs almost spontaneously, and in which emission from a luminescent substance ceases when the exciting source is removed. In fluorescent materials, the excited state has the same spin as the ground state. A compound capable of fluorescence is termed a "fluor".

The term "phosphorescence", as used herein, refers to a quasi-stable electron excitation state involving a change of spin state (intersystem crossing) which decays only slowly. In phosphorescence, light emitted by an atom or molecule persists after the exciting source is removed. It is similar to fluorescence, but the species is excited to a metastable state from which a transition to the initial state is forbidden. Emission occurs when thermal energy raises the electron to a state from which it can de-excite. Therefore, phosphorescence is temperature-dependent. The term phosphorescence thus refers to a delayed luminescence or sustained glowing after exposure to energized particles such as electrons or ultraviolet photons, that is, a luminescence that persists after removal of the exciting source. It is sometimes called afterglow. A compound capable of phosphorescence is termed a "phosphor".

The phosphorescent materials useful in aspects of the present invention include zinc sulphide and strontium aluminate or of strontium oxide aluminate, with a luminance approximately 10 times greater than zinc sulphide. Strontium aluminate based afterglow pigments are marketed under brand names like Super-LumiNova or NoctiLumina. Other suitable phosphors are for instance described in U.S. Pat. No. 5,424,006.

The phosphorescent marker as referred to herein is commonly referred to as a "phosphor". A phosphor is a substance that exhibits the phenomenon of phosphorescence. Phosphors are transition metal compounds or rare earth compounds of various types. The most common uses of phosphors are in Cathode ray tubes (CRT) displays and fluorescent lights. CRT phosphors were standardized and designated by the letter "P" followed by a number. Phosphors are usually made from a suitable host material, to which an activator is added. The best known type is a copper-activated zinc sulphide and the silver-activated zinc sulphide. Suitable host materials are typically oxides, nitrides and oxynitrides, sulphides, selenides, halides or silicates of zinc, cadmium, manganese, aluminum, silicon, or various rare earth metals. The activators prolong the emission time (afterglow). In turn, other materials (eg. nickel) can be used to quench the afterglow and shorten the decay part of the phosphor emission characteristics. All of the above phosphors are suitable for use in the present invention. Thus, the phosphorescent materials useful in aspects of the present invention include zinc sulphides and strontium aluminates, with a luminance approximately 10 times greater than zinc sulphide. Strontium aluminate based afterglow pigments are marketed under brand names like Super-LumiNova or NoctiLumina. Other suitable phosphors are for instance described in U.S. Pat. No. 5,424, 006.

Other suitable compounds include $SrAl_2O_4:Eu,Dy$ or Europium/Dysprosium-activated (or doped) strontium aluminate and $Sr_2MgSi_2O_7:Eu^{2+}$; $Dy^{3+}$ or Europium/Dysprosium-doped strontium magnesium silicate. Doping may for instance also occur with Terbium ($Tb^{3+}$). Doping may occur with any one individual or a combination of activators (co-doping). Usually, the phosphors are in particulate form (as powders) usually with a particle sixe of 1-100 µm, preferably 15-25 µm. In alternative preferred embodiments nanometer-sized particles (10-500 nm) can be used.

The commonly quoted parameters for phosphors are the wavelength of emission maximum (in nanometers, for instance 200-450 nm for strontium aluminate and zinc sulphide, or alternatively color temperature in Kelvins for white blends), the peak width (in nanometers at 50% of intensity), and decay time or afterglow extinction (in seconds or minutes). The emission wavelength for strontium aluminate and zinc sulphide is usually 520-530 nm (yellowish-green), although other colours may also be obtained, The phosphor for use in aspects of the present invention is not particularly limiting to any particular type.

This phosphorescent marker can be used at extremely low concentrations, in the order of parts per million (ppm) to parts per billion (ppb). Preferably the concentration or amount used of the phosphorescent marker is 0.01-100 ppb (or µg/kg of coating) or even lower.

The excitation of the phosphorescent marker may require a separate excitation wavelength, but identical excitation wavelengths may also be used.

The at least one phosphorescent marker may be provided at different concentrations relative to the coating substance to suit the required detection limit for the phosphorescent marker in the coating and determine the optimal coating composition. Alternatively, the concentrations of one phosphorescent marker may be varied relative to another phosphorescent marker in the coating composition. Alternatively, the concentration of multiple phosphorescent marker may be held constant. It is an advantage of using different concentrations that the differentiating capacity of the different markers can be used as an additional improvement of the sensitivity and accuracy of the measurement. It is an advantage of using different phosphorescent markers that the quantitative contribution of individual components of a coating composition that consists of multiple components can be checked in the final coating when different markers are added to individual components. The measurement of the different concentrations (as phosphorescence intensities) can be used as a method to quantify the amount of certain coating components relative to other coating components, for example certain components in a seed treatment product (such as a fungicide, an insecticide, etc) that will be applied to the seed. The intensities can be used as an estimation of the quantity of those chemicals applied to the seeds. For this purpose, at least one of the markers may be provided in combination with a surface treatment (that is, mixed with the treatment formulation) in order to quantitatively or qualitatively monitor the result of the surface treatment in terms of amount of formulation applied to the surface.

The markers may be provided to the seed in several ways. For instance one may treat the seeds such that the marker is provided on the seeds pericarp. Alternatively the marker may be provided as (part of) a seed treatment process, including but not limited to, a seed coating, seed encrusting and/or seed pelleting. The term seed coating as used herein is intended to cover all treatments of seed as described herein. Express reference is made to the patent documents listed in the Introduction for general teachings of applying a coating to seed and seed coat composition.

An important advantage of the present invention is that the marking system can be used to quantify the binder, biologically active agent, for instance biocides, nutrients and soil conditioners, and miscellaneous adjuvants or excipients, in a seed coat or seed crust, i.e. to monitor the efficacy and accuracy of the seed treatment process. Any one individual marker of a marker system of the present invention may be provided in a pre-determined quantity to serve as an internal standard for monitoring the amount of other agents in the seed coat. This system may be used to monitor the amount of treatment substance successfully loaded on a set amount (e.g. per kilogram) of seed as a result of a coating process, which amount is referred to as the recovery. Alternatively, this system may be used to monitor the amount of treatment substance successfully loaded on individual seeds as a result of a coating process, which amount is referred to as the distribution. Hence, the present invention provides for a method of determining the recovery and/or distribution of seed coat substance (binder, biologically active agent, for instance biocides, nutrients and soil conditioners, and miscellaneous adjuvants or excipients, in a seed coat or seed crust) as quality parameters of a seed treatment process. The method comprises the co-application of the marker-system of the present invention with the seed coat substance, preferably as a mixture, and the determination of the amount of at least one marker of said marker system present in the resulting seed coat. Comparing the presence of the amount of the marker in the coat on the basis of individual seeds or on the basis of a set amount (weight) of seeds provides a measure of, respectively, the distribution and recovery. In such aspects, the marker is provided to the seed (or generally, the product) as part of a seed- (product-) treatment process, and wherein the intensity of said marker is used to monitor the quality of the seed- (product-) treatment process.

An important advantage of the present invention is that the marking system can be used to quantify the binder, biologically active agent, for instance biocides, nutrients and soil conditioners, and miscellaneous adjuvants or excipients, in a seed coat or seed crust, i.e. to monitor the efficacy and accuracy of the seed treatment process. Any one individual marker of a marker system of the present invention may be provided in a pre-determined quantity to serve as an internal standard for monitoring the amount of other agents in the seed coat. This system may be used to monitor the amount of treatment substance successfully loaded on a set amount (e.g. per kilogram) of seed as a result of a coating process, which amount is referred to as the recovery. Alternatively, this system may be used to monitor the amount of treatment substance successfully loaded on individual seeds as a result of a coating process, which amount is referred to as the distribution. Hence, the present invention provides for a method of determining the recovery and/or distribution of seed coat substance (binder, biologically active agent, for instance biocides, nutrients and soil conditioners, and miscellaneous adjuvants or excipients, in a seed coat or seed crust) as quality parameters of a seed treatment process. The method comprises the co-application of the marker-system of the present invention with the seed coat substance, preferably as a mixture, and the determination of the amount of at least one marker of said marker system present in the resulting seed coat. Comparing the presence of the amount of the marker in the coat on the basis of individual seeds or on the basis of a set amount (weight) of seeds provides a measure of, respectively, the distribution and recovery.

The present invention further provides a marker composition comprising the marker system of the present invention in a suitable carrier system. The marker composition may be a liquid or solid composition. Preferably the carrier system is a liquid carrier or diluent, for instance a (colourless) polymer. Such polymers are well known in the art. Alternatively, the carrier may be a powder. In yet a further alternative, the carrier may be a combination of a liquid and a powder. The powder may for instance be an encrusting powder for providing a seed coat. Such powders are well known in the art.

Preferably the carrier is an agronomically acceptable carrier. By "agronomically acceptable carrier" is meant any substance which can be used to aid the dispersion of the active ingredient without impairing the active ingredient's effectiveness and which by itself has no significant detrimental effect on the soil, equipment, desirable plants, or the agronomic environment. A very suitable agronomically acceptable carrier is water. Other suitable carriers are solid carriers such as in the form of coating polymers or coating powdered as described in more detail herein below.

Thus, the marker system of the present invention is preferably provided dissolved or suspended in a polymer matrix. Preferably said polymer is a liquid form which can be applied to the product. For instance, the product may be coated by painting, printing, submerging or otherwise applying the marker composition to a surface of the product. Seeds may for instance be coated with the marker by mixing a batch of seed (for instance an amount of 1-10 tons) with the marker composition (for instance 1 L of a liquid polymer composition comprising the markers system) and allowing for the seeds to become coated with the composition. Methods for coating seeds are well known in the art and need not be described in detail here.

Seeds are often treated to reduce yield losses during cultivation and for enhancing the agronomic and nutritional value of the produce. Such treating agents are for example fungicides, insecticides, rodenticides, nematocides, miticides or bird repellents. Furthermore, many varieties of genetically altered crops are coming to the market. Treated and/or genetically modified seeds must be marked in order to distinguish them from the untreated and unmodified seeds. The marking of seeds is particularly beneficial for farmers who then can easily distinguish the chemically treated and modified seeds for plantings from e.g. cereal grains for consumption.

In addition to the at least one marker, the coating composition for coating a product, preferably seeds, may contain one or more of a binder, biologically active agent, for instance biocides, nutrients and soil conditioners, and miscellaneous adjuvants or excipients, as is well known to those skilled in the art. The binder is preferably a film forming or adhesive component capable of securing the coating composition to the surface of the product, for example poly(vinyl alcohol), cellulosic polymers and derivatives, such as carboxymethylcellulose, hydroxyethylcellulose, poly(acrylic acid), polyacrylamide, poly (acrylamide/acrylic acid) copolymer, ethylene oxide/propylene oxide copolymers which are solid at 25° C., and water-soluble cellulose ether, vinyl acetate, low melting polyesters, such as poly-e-caprolactone, polymers and copolymers containing 2-propenenitrile or 2-methyl-2-propenenitrile, gelatin and lignosulfonates. Preferably, the binder is a water-soluble, film forming polymer.

The biologically active agent may be an agent selected to protect the seed from pests, fungi or birds, such as an antimicrobial agent, pesticide, fungicide or repellant. The nutrients and soil conditioning agents are selected to promote germination and/or growth, such as lime, trace elements, hormones, vitamins, fertilizer, and urea.

The miscellaneous adjuvants include wetting agents, surfactants, dispersing agents: stabilizers, drying agents, such as aluminosilicates, opacifying agents, fillers, plasticizers and various compounds which are intended to enhance the performance of the binder such as .varies.-cellulose, lactose and ethylene glycol.

A typical composition comprises the marker system of the invention in a concentration of from 0.01 to 1000 ppm of the phosphorescent marker based on the weight of the composition, in particular from 0.1 to 100 ppm. The skilled person will understand that the exact amount of the marker system in the composition will depend on the quality of the coating composition if not ready-mixed, the general quality of the coating obtained by the end user, the shielding of the markers by other substances in the coating, the type of coating (crust or thin-film), the matrix or carrier used, the loading level of the coating (thickness or amount applied to product), etc.

In addition, the skilled person will understand that the contribution of each of the individual markers in the marker system will be determined by the level of information required or aimed to be obtained by the analysis as well as by the requirement to provide reliable results.

Preferably, in order to be as cost-effective as possible, a marker composition comprises the markers in very low dosages, as the active compounds are the most costly of the composition. Generally an amount of the phosphorescent marker of about 5 to 10 ppm is sufficient to provide for a detectable amount of the marker on the product, when 1 L of the marker composition is mixed with 10 tons of seed. The concentration of active ingredient in a deliverable or ready for use formulation may vary in a wide range and may be as low 0.0000001 wt. % and as high as 99 wt %.

Information provided by the marking system may include (coding) reference to such information as production years (different codes for different years), different lines of hybrids, male/female distinction, geographical area, chemical treatments of the seed (e.g. antimicrobial agent, pesticide, fungicide or repellent, nutrients and soil conditioning agents, such as lime, trace elements, hormones, vitamins, fertilizer, and urea). It is a particular aim of the present marking system that the quantitative nature allows for the evaluation of the quality of the said treatment, that is, whether the chemical has been provided to the seed in a sufficient quantity.

The coating composition of the present invention allows for the evaluation of the quality of the coating process and of the resulting coating, while at the same time providing a means to identify that product, whereas it is itself difficult to detect. It is an advantage of the use of the phosphorescent markers that neither can be detected when irradiated by light of the visible spectrum in the presence of the illumination source when the concentration of the phosphor is lower than the scattering or autofluorescence emitted by the object marked with the phosphorescent marker and/or background radiation. Hence the marking of the product cannot be detected unless scanned for by using dedicated detection equipment and an intermittent illumination regime that allows for detection of the phosphor-specific emission.

Thus, the phosphorescent marker system of the present invention allows for the presence of phosphorescent markers which can only be detected when excitation irradiation is interrupted and phosphorescence resulting from said excitation is measured in the absence of excitation irradiation.

It is possible to use such low marker concentrations that specific emission levels are lower than autofluorescence emitted by the object marked with the phosphorescent marker and/or background radiation. This makes it virtually impossible to detect the marker, unless it is known that the marker is there and the observer knows what to look for. It is preferred that very low levels of the phosphorescent markers are used (such as below 1 ppm, for instance 0.001-0.99 ppm), because such low levels cannot be detected under continuous excitation irradiation due to high background irradiation levels. This provides for a secret or difficult-to-detect marker system. In alternative embodiments, levels of the phosphorescent markers may suitably range from 1-1000 ppm.

The invention claimed is:

1. A method to assess the quality of a surface coating process or of the surface coating resulting therefrom, wherein said assessing comprises the steps of:
producing said surface coating by applying to the surface of said product a coating composition comprising an aqueous suspension comprising a coating substance and a marker system comprising at least one phosphorescent marker, wherein the coating substance and the phosphorescent marker are present at a fixed ratio, and wherein the marker system serves as an internal standard to the coating substance, and
optionally drying said coating composition;
quantitatively or qualitatively measuring the intensity of said at least one phosphorescent marker in said surface coating on the surface of said product; and
determining from the measured intensity of the phosphorescent marker the amount of coating substance on said product surface thereby assessing the quality of said surface coating or of said surface coating process, wherein said product is a seed and wherein said surface coating process comprises the application of a desired amount or concentration of a seed coat to said seed.

2. The method of claim 1, wherein said fixed ratio of the phosphorescent marker to the coating substance is in the range of $1:1\times10^1$ to $1:1\times10^9$.

3. The method of claim 1, wherein said marker system is provided at an amount that results in a phosphor-specific emission below background radiation or autofluorescence emitted from said product.

4. The method of claim 3, wherein said background radiation comprises light having a wavelength equal to the excitation wavelength and/or emission wavelength of said phosphor.

5. The method of claim 4, wherein said light having a wavelength equal to the emission wavelength of said phosphor is autofluorescence under daylight conditions (400-20000 lux).

6. The method of claim 1, wherein said marker is applied to said surface at an amount of between 0.001 and 999 ppm.

7. The method of claim 1, wherein the intensity of said marker is used to monitor the surface coating process during the application of the coating substance.

8. The method of claim 1, wherein the quality of said surface coating process is the recovery and/or distribution of coating substance on the surface of said product.

9. The method of claim 1, wherein said phosphorescent marker is selected from the group consisting of europium-, dysprosium-, and/or terbium-doped lutetium orthophosphate ($LuPO_4$:Eu/Dy/Tb); europium-, dysprosium-, and/or terbium-doped strontium aluminate ($SrAl_2O_4$:Eu/Dy/Tb); europium-, dysprosium-, and/or terbium-doped strontium magnesium silicate ($Sr_2MgSi_2O_7$:Eu/Dy/Tb), copper-activated zinc sulphide (ZnS:Cu); silver-activated zinc sulphide (ZnS:Ag); copper-activated zinc-cadmium sulphide ((Zn,Cd)S:Cu); bismuth-activated calcium-strontium sulphide ((Ca,Sr)S:Bi) and combinations thereof.

10. The method of claim 1, wherein said coating substance is selected from the group consisting of antimicrobial agents, pesticides, fungicides, herbicides, rodenticides, nematocides, miticides, bird repellents, insect repellents nutrients (including N, P or S), organic fertilizers, lime, trace elements, hormones, vitamins, fertilizers, pigments, dyes, urea and combinations thereof.

11. Kit of parts, comprising
(a) a seed coating composition comprising an aqueous suspension of a seed coating substance and a marker system comprising at least one phosphorescent marker, wherein the coating substance and the phosphorescent marker are present at a fixed ratio, wherein said fixed ratio of the phosphorescent marker to the coating substance is in the range of $1:1\times10^1$ to $1:1\times10^8$, and wherein the marker system serves as an internal standard to the coating substance, wherein said marker system is provided in a container optionally in combination with the coating substance, and
(b) a detector system configured to detect the presence of said phosphorescent marker on a seed surface, said detector comprising an excitation source and a detector configured to detect phosphorescence emitted from said phosphorescent marker, and a control unit configured to switch said excitation source between an on position and an off position and activate said detector when the excitation source is switched off after excitation of said seed thereby measuring phosphorescence emission, the detector further configured to determine the measured intensity of the phosphorescent marker the amount of coating substance on said seed surface thereby assessing the quality of said seed surface coating or of said seed surface coating process, said kit further optionally comprising
(c) a carrier or diluent for applying the marker to the product and/or
(d) instructions for the applying said marker to a product, for operating said detector and for the analysis of said marked product.

12. The kit of claim 11, wherein in said seed coating composition said phosphorescent marker is provided as phosphor particles having an average particle size of between 10 and 40 microns.

13. The kit of claim 11, wherein in said seed coating composition said phosphorescent marker is selected from the group consisting of europium-, dysprosium-, and/or terbium-doped lutetium orthophosphate ($LuPO_4$:Eu/Dy/Tb); europium-, dysprosium-, and/or terbium-doped strontium aluminate ($SrAl_2O_4$:Eu/Dy/Tb); europium-, dysprosium-, and/or terbium-doped strontium magnesium silicate ($Sr_2MgSi_2O_7$:Eu/Dy/Tb), copper-activated zinc sulphide (ZnS:Cu); silver-activated zinc sulphide (ZnS:Ag); copper-activated zinc-cadmium sulphide ((Zn,Cd)S:Cu); bismuth-activated calcium-strontium sulphide ((Ca,Sr)S:Bi), and combinations thereof.

14. The kit of claim 11, wherein in said seed coating composition said coating substance is selected from the group consisting of one or more antimicrobial agents, pesticides, fungicides, herbicides, rodenticides, nematocides, miticides, bird repellents, insect repellents, nutrients (including N, P or S), organic fertilizers, lime, trace elements, hormones, vitamins, fertilizers, pigments, dyes, urea and combinations thereof.

15. A coated seed comprising a seed coat produced by applying the seed coating composition described in claim 11 and drying said seed coating composition.

* * * * *